United States Patent [19]

Wurtman et al.

[11] Patent Number: 5,019,594
[45] Date of Patent: May 28, 1991

[54] METHOD FOR DECREASING APPETITE

[75] Inventors: Richard J. Wurtman, Boston; Timothy J. Maher, Milton, both of Mass.

[73] Assignee: Interneuron Pharmaceuticals, Inc., New York, N.Y.

[21] Appl. No.: 442,011

[22] Filed: Nov. 28, 1989

[51] Int. Cl.$^5$ ................ A61K 31/195; A61K 31/535; A61K 31/42

[52] U.S. Cl. .................. 514/561; 514/231.2; 514/374

[58] Field of Search ...................... 514/561, 374, 231.2

[56] References Cited

U.S. PATENT DOCUMENTS

| 4,327,112 | 4/1982 | Wurtman | 514/567 |
| 4,598,094 | 7/1986 | Wurtman et al. | 514/561 |
| 4,673,689 | 6/1987 | Wurtman et al. | 514/561 |
| 4,885,312 | 12/1985 | Wurtman et al. | 514/561 |

OTHER PUBLICATIONS

Chemical Abstracts (vol. 68, No. 93260b), 1968.
Chemical Abstracts (vol. 102, No. 17558k), 1985.

*Primary Examiner*—Stanley J. Friedman
*Assistant Examiner*—Kevin Weddington
*Attorney, Agent, or Firm*—Alan H. Levine

[57] ABSTRACT

A composition for decreasing appetite comprising an indirect-acting sympathomimetic drug and tyrosine or a tyrosine precursor. The drug may be phenylpropanolamine, amphetamine, or ephedrine. The tyrosine enhances the known appetite-suppressing activity of the drug.

5 Claims, 2 Drawing Sheets

METHOD FOR DECREASING APPETITE

This invention relates to appetite suppression, for weight control purposes, employing indirect-acting sympathomimetic drugs or amines.

A number of such drugs, e.g., phenylpropanolamine, amphetamine, and ephedrine, are traditionally used to suppress appetite, as well as for other purposes. A problem recognized in the past which is associated with use of some indirect-acting sympathomimetic drugs is that after a few doses, they often stop functioning, i.e., tachyphylaxis sets in. U.S. Pats. Nos. 4,598,094 and 4,673,689 deal with this problem and disclose prevention of tachyphylaxis by administering tyrosine or a tyrosine precursor together with indirect-acting sympathomimetic drugs such as ephedrine, phenylpropanolamine, and amphetamine. These patents make no reference whatsoever to combining any of these drugs and tyrosine for appetite-suppression purposes.

The present invention is based on a realization that tyrosine, or a tyrosine precursor, can be used to potentiate the appetite reduction activity of indirect-acting sympathomimetic drugs.

It is an object of the invention to provide a composition comprising an indirect-acting sympathomimetic drug capable of performing an appetite suppressing function, and tyrosine or a tyrosine precursor.

It is another object of the invention to provide a method of decreasing appetite by administering both an indirect-acting sympathomimetic drug capable of performing an appetite-suppressing function, and tyrosine or a tyrosine precursor.

Figure 1:
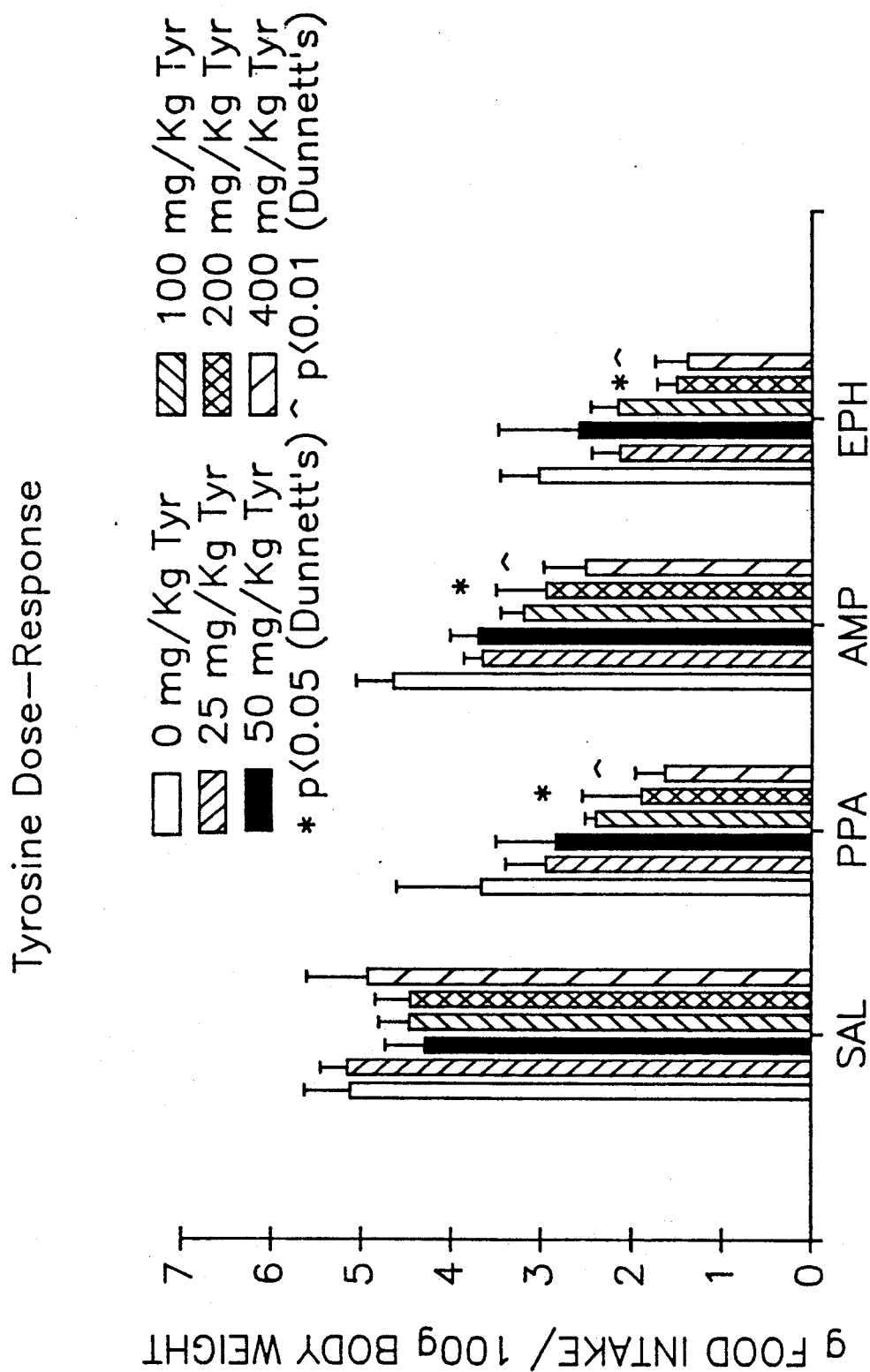
Figure 2:
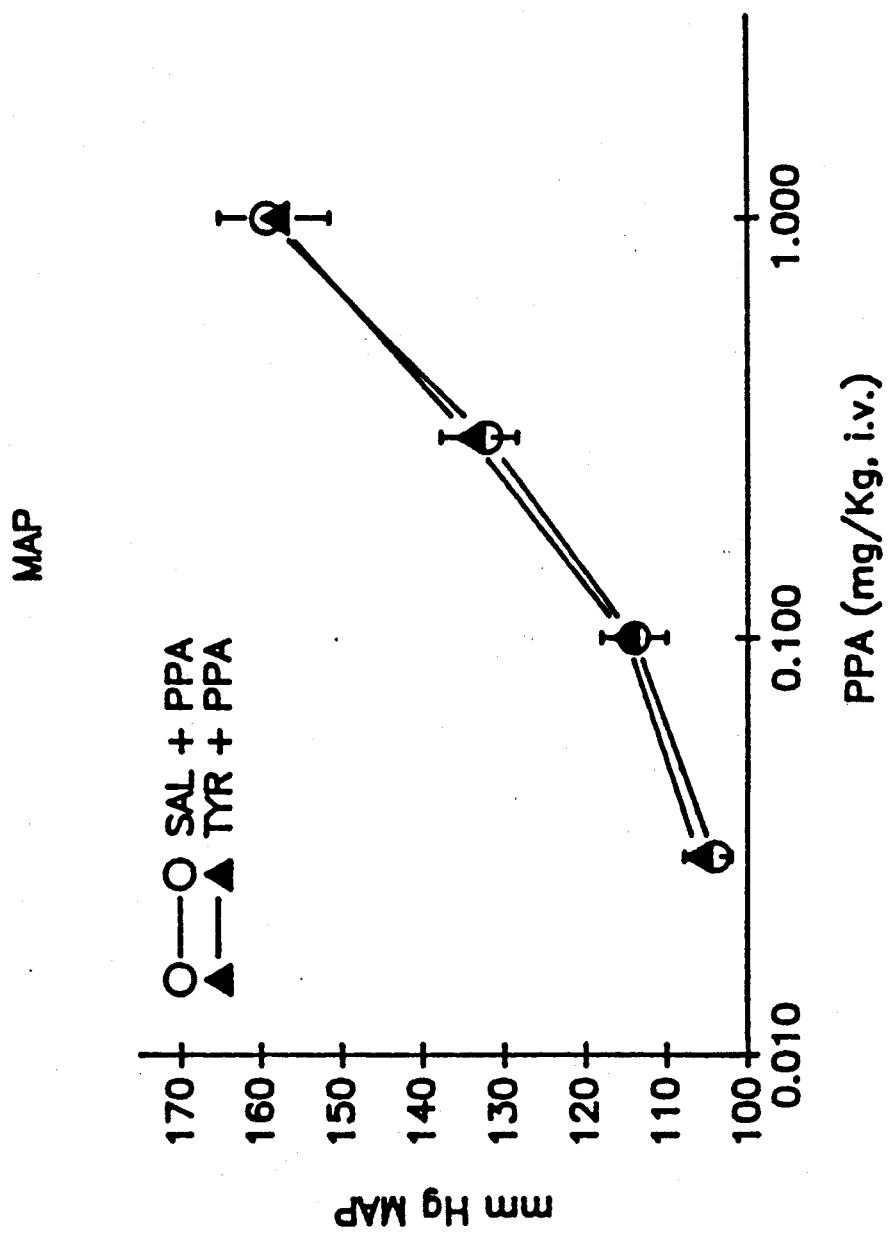

In the accompanying drawings:

FIG. 1 is a bar graph showing the effect different quantities of tyrosine, combined with each of saline solution, phenylpropanolamine, amphetamine, and ephedrine have on the quantity of food consumed by rats; and FIG. 2 is a graph illustrating the effect on blood pressure of rats to which the combination of saline and phenylpropanolamine, and the combination of tyrosine and phenylpropanolamine, have been administered.

The term "indirect-acting sympathomimetic drug" is intended to include within its scope both indirect-acting drugs and mixedacting drugs having both indirect-acting and direct-acting components. Direct-acting drugs, as their name implies, act directly on sympathomimetic nerve receptors. Indirect-acting drugs cause the nerve cells to release a product which then acts on the nerve receptors.

While the precise mechanism by which the present invention produces the desired function is not entirely clear, it is known that indirect-acting sympathomimetic amine drugs cause nerve endings to release norepinephrine and dopamine. Tyrosine and tyrosine precursors, such as phenylalanine and tyrosine-containing peptides, also can enhance the release of norepinephrine and dopamine from sympathetic neuron synapses. Thus, it is theorized that combining tyrosine or a tyrosine precursor with a sympathomimetic drug produces a synergistic, or at least additive effect, which increase the anorectic activity of a given dose of the drug.

Consequently, the present invention can be used either to increase the appetite-suppression effect of such a drug without increasing the amount of the drug which is administered, or the same appetite-suppression effect can be obtained by administering a lower dosage of the drug.

Indirect-acting sympathomimetic amine drugs commonly used for appetite suppression are phenylpropanolamine (PPA) amphetamine, and ephedrine. Other drugs useful for the purpose are pseudoephedrine, norpseudoephedrine, diethylpropion, benzphetamine, phendimetrazine, phenmetrazine, phentermine, chlorphentermine, and aminorex. For appetite suppression purposes, these drugs are usually administered orally, but in some circumstances they may be administered parenterally, i.e., intravenously, or in any other effective manner, e.g., nasally.

The drugs are administered to a human patient within a preferred range of dosage levels which are readily found in the standard literature available to practitioners in the field of weight control. For example, PPA is usually administered in dosages of 5 to 25 milligrams (mg) three times per day, i.e., daily dosages of 15 to 75 mg; amphetamine is usually administered in dosages of 1.25 to 10 mg three times per day, i.e., daily dosages of 3.75 to 30 mg; and ephedrine is usually administered in dosages of 5 to 50 mg per day, i.e., daily dosages of 15 to 150 mg. Other drugs used for appetite reduction are administered in dosages as low as 3 mg/day and as high as 150 mg/day.

The amount of tyrosine or tyrosine precursor administered to a human patient is in the range of 250 mg to 15 grams (g), preferably between 1 g and 5 g, per day. Use of less than 250 mg of tyrosine for an adult human is believed to have little or no measurable effect. Dosages of more than 15 g of tyrosine are believed to enter the range in which no appreciable additional advantage is obtained by increases in dosage level. The tyrosine or tyrosine precursor can be administered as free amino acids, peptides, esters, salts, natural or synthetic polymers, or constituents of foods. The route of administration can be oral or parenteral, or any other effective manner. Any suitable tyrosine precursor can be employed, such as a low dose of phenylalanine, i.e., 500 mg or less.

The following example illustrates that administering tyrosine to an animal together with an indirect-acting sympathomimetic amine drug significantly potentiates the anorexic activity of the drug as compared to administration of tyrosine and a saline solution. Moreover, the anorexic activity is dose-dependent, i.e., the more tyrosine administered, the greater the appetite reduction effect.

EXAMPLE I

Rats were housed individually in suspended wire mesh cages and maintained on the following reversed 12 hour lights on / lights off schedule: lights on from 2100 hrs (9 PM) to 900 hrs (9 AM), lights off from 900 hrs to 2100 hrs. For four days prior to the start of the experiment, the rats were given free access to rodent chow pellets. On the day of the experiment, the procedure was as follows:

800 hrs - the food was removed and the rats were weighed;

900 hrs - lights off; rats have free access to water;

1300 hrs different groups of rats were injected intraparenterally with different dosages of tyrosine, the dosages being 25 mg per kilogram (kg) of body weight, 50 mg/kg, 100 mg/kg, 200 mg/kg, and 400 mg/kg. As a control, one group of rats was injected with saline. At the same time, subgroups of rats within each group were injected with PPA (20 mg/kg), d-amphetamine (1.75 mg/kg), or 1-ephedrine (20 mg/kg). As a control one subgroup within each group was injected with saline;

1400 hrs - each rat was given free access to a preweighed amount of food, the food being a mush diet of 50% ground rodent chow and 50% of a 4% nutrient agar solution, plus tap water. The preweighed food was contained in glass jars and a clean sheet of paper was placed under each cage to catch spillage;

1530 hrs - the food was removed and weighed to determine how much was consumed.

The results are indicated in FIG. 1. It will be seen that when tyrosine is administered with saline, which is inactive from the point of view of appetite reduction, no significant decrease, and in some cases no decrease at all, in food intake is observed as the dose of tyrosine is increased. However, when tyrosine is combined with PPA, amphetamine, or ephedrine, as the dosage of tyrosine is increased, in general the amount of food intake decreases although the doses of the drugs remain unchanged. This clearly shows the increased appetite-suppression effect of each drug, when used together with tyrosine, without increasing the dosage of the drug. It follows, also, that the same appetitesuppression effect of a particular dose of drug can be obtained with a lower dose of the drug when used together with tyrosine.

U.S. Patent No. 4,327,112 deals with increasing blood pressure, in a patient having low blood pressure, by administering tyrosine to the patient either alone or in combination with a drug which increases noradrenergic neurotransmission in the sympathetic nervous system. Therefore, the following example illustrates the failure of tyrosine to potentiate the pressor effects of phenylpropanolamine in normotensive rats.

EXAMPLE II

Rats were anesthetized with chloralose and urethane, and two groups of such rats were pretreated intraparenterally with 200 mg/kg of L-tyrosine or saline, respectively. The right common carotid artery and the left external jugular of each rat were cannulated. One hour after pretreatment, PPA was administered intravenously in a volume of one milliliter/kg of body weight. After the blood pressure returned to normal, increasing doses were administered. As indicated in FIG. 2, no significant effect on blood pressure was observed due to use of tyrosine. While the mean arterial blood pressure (MAP), i.e., the average systolic and diastolic pressure, does increase with increasing doses of PPA, the combination of tyrosine with PPA does not effect any significant additional increase in blood pressure as compared to the use of saline with PPA.

The reason for this result probably lies in the fact that tyrosine appears to have the ability to increase blood pressure when blood pressure is low, and to decrease blood pressure when blood pressure is high. Thus, when blood pressure is normal, or has been elevated by administration of a drug together with tyrosine, tyrosine will have little or no effect on blood pressure. Moreover, in the cardiovascular system, the action of PPA is direct, and thus would not be expected to be enhanced by a treatment that increases presynaptic norepinephrine or dopamine levels.

The invention has been shown and described in preferred form only, and by way of example, and many variations may be made in the invention which will still be comprised within its spirit. It is understood, therefore, that the invention is not limited to any specific form or embodiment except insofar as such limitations are included in the appended claims.

We claim:

1. A method of decreasing appetite in an animal by administration of an appetite-suppressing drug so as to produce a greater appetite-suppressing effect than that produced by administration of the drug alone, comprising administering to the animal an indirect-acting sympathomimetic drug capable of performing an appetite-suppressing function, and tyrosine or a tyrosine precursor wherein the drug and tyrosine are administered in an amount equal to 3 to 150 mgs of the drug and 250 mgs to 15 grams of tyrosine, per day.

2. A method as defined in claim, 1 wherein the tyrosine precursor is a tyrosine-containing peptide.

3. A method as defined in claim 1 wherein the indirect-acting sympathomimetic drug is selected from the group consisting of ephedrine, amphetamine, phenylpropanolamine, pseudoephedrine, norpseudoephedrine, diethylpropion, benzphetamine, phendimetrazine, phenmetrazine, phentermine, chlorphentermine, aminorex, and combinations thereof.

4. A method as defined in claim 1 wherein the indirect-acting sympathomimetic drug is selected from the group consisting of phenylpropanolamine, amphetamine, and ephedrine, and combinations thereof.

5. A method as defined in claim 1 wherein the ratio of tyrosine or tyrosine precursor to the indirect-acting sympathomimetic drug is large enough to enhance the appetitesuppressing effect of the drug.

* * * * *